United States Patent [19]

Correia et al.

[11] Patent Number: 5,227,549
[45] Date of Patent: Jul. 13, 1993

[54] SYNTHESIS OF 1,2-DICHLOROETHANE BY CCL₄ OXYCHLORINATION OF ETHYLENE

[75] Inventors: Yves Correia, Chateau Arnoux; Gerard Chastel, Sisteron, both of France

[73] Assignee: Elf Atochem S.A., Puteaux, France

[21] Appl. No.: 835,868

[22] Filed: Feb. 18, 1992

[30] Foreign Application Priority Data

Feb. 15, 1991 [FR] France .............................. 91-01824

[51] Int. Cl.⁵ ........................................... C07C 17/156
[52] U.S. Cl. .................................... 570/243; 570/251
[58] Field of Search .............................. 570/243, 251

[56] References Cited

U.S. PATENT DOCUMENTS

| | | | |
|---|---|---|---|
| 3,883,605 | 5/1975 | Antonmi et al. | 570/243 |
| 4,754,088 | 6/1988 | Schmidhammer et al. | 570/243 |
| 4,849,562 | 7/1989 | Buhs et al. | 570/243 |

FOREIGN PATENT DOCUMENTS 1351700 9/1971 United Kingdom .

*Primary Examiner*—Werren B. Lone
*Attorney, Agent, or Firm*—Burns, Doane, Swecker & Mathis

[57] ABSTRACT

A major amount of 1,2-dichloroethane (D12) and lesser amounts of trichloroethane and tetrachloroethane are prepared by contacting carbon tetrachloride, ethylene and oxygen (or an oxygen-containing gas, notably air) with an oxychlorination catalyst at a temperature sufficient to produce D12, and thereafter separating such D12 from the products of reaction.

7 Claims, No Drawings

SYNTHESIS OF 1,2-DICHLOROETHANE BY CCL₄ OXYCHLORINATION OF ETHYLENE

BACKGROUND OF THE INVENTION

1. Field of the Invention

The present invention relates to the synthesis of 1,2-dichloroethane by oxychlorination of ethylene by means of carbon tetrachloride.

2. Description of the Prior Art

It is known to this art that chlorination of ethylene produces 1,2-dichloroethane (D12) which, by simple pyrolysis, is converted into vinyl chloride (VCM) and hydrochloric acid (HCl). HCl is recycled to produce D12 according to the following oxychlorination reaction mechanism (1):

$$2C_2H_4 + O_2 + 4\ HCl \rightarrow 2C_2H_4Cl_2 + 2\ H_2O \qquad (1)$$

This oxychlorination reaction makes it possible to utilize the chlorine contained in the HCl.

The above processes are described in Ullmann's *Encyclopedia Of Chemical Industry*, 5th edition, volume A 6, pages 263–270 and 283–291.

French Patent No. 2,260,551 describes the oxychlorination of heavy chlorinated residues, namely, the reaction between these residues of ethylene and oxygen to produce perchloroethylene, trichloroethane, tetrachloroethane and D12.

South African Patent Application No. 71-5,781, published Mar. 27, 1972, describes a process for the oxychlorination of ethylene, to prepare a mixture of perchloroethylene and trichloroethylene.

According to this prior art, the ethylene, the oxygen and the chlorine are passed over a fluidized bed catalyst based on copper chloride deposited onto a porous support, at a temperature ranging from 410° to 440° C. The reaction is carried out in the presence of carbon tetrachloride originating from the recycling of the products exiting the fluidized bed. The products exiting the fluidized bed are cooled to condense perchloroethylene, trichloroethylene and carbon tetrachloride. The latter (CCl₄) is mixed with the feed gases (C₂H₄, Cl₂ and air) and is thus recycled to the fluidized bed. The perchloroethylene and trichloroethylene constitute at least 50 mol % of the chlorinated products exiting the fluidized bed. The amount of CCl₄ is constant and the CCl₄ does not accumulate. Its concentration does not exceed 10 mol % relative to the organic compounds charged into the fluidized bed, and this corresponds to a few percent relative to the total amount of the inlet gases. The amount of chlorine, in the form of Cl₂, ranges from 40% to 75% of the chlorine-containing reactants introduced into the fluidized bed, about 2% to 8% is in the form of HCl and the remainder is organic chlorine-containing compounds (including CCl₄). The atomic ratio of oxygen to carbon at the inlet to the fluidized bed ranges from 0.85 to 2. The overall result of this reaction, accordingly, is to produce perchloroethylene and trichloroethylene while consuming ethylene, chlorine (Cl₂) and oxygen.

SUMMARY OF THE INVENTION

Accordingly, a major object of the present invention is the provision of an improved process for the preparation of 1,2-dichloroethane (D12) and lesser amounts of its higher homologs, while consuming ethylene, CCl₄ and oxygen, according to the following reaction mechanism (2):

$$CCl_4 + 2\ C_2H_4 + O_2 \rightarrow 2\ C_2H_4Cl_2 + CO_2 \qquad (2)$$

Another object of this invention is the provision of such improved oxychlorination process that utilizes the chlorine content of the CCl₄. Indeed, during the synthesis of the chloromethanes, CCl₄ is inevitably produced in too great an amount. Thus, it has now been determined that such CCl₄ can itself be used as a source of chlorine in an ethylene oxychlorination reaction, namely, a mixture of CCl₄, C₂H₄ and O₂ (or air) can be passed over an oxychlorination catalyst to produce D12 and, in lesser amounts, its higher homologs such as trichloroethane and tetrachloroethane.

Briefly, the present invention thus features a process for the synthesis of 1,2-dichloroethane, by contacting carbon tetrachloride, ethylene and oxygen with an oxychlorination catalyst at a temperature sufficient to form 1,2-dichloroethane, and thereafter separating said D12 from the products of reaction.

DETAILED DESCRIPTION OF THE PREFERRED EMBODIMENTS OF THE INVENTION

More particularly according to the present invention, the subject reaction is carried out under normal conditions of oxychlorination in a fixed or fluid bed, over any catalyst based on alumina, silica magnesia or attapulgite and containing copper, but which may also contain the usual additives, potassium, magnesium and rare earths.

Suitable such catalysts are described, for example, in French Patents Nos. 1,555,518, 2,260,551, 2,063,365, 2,213,259 and 2,141,452, and European Patents Nos. 255,156, 257,561 and 176,432.

These catalysts generally comprise copper chloride deposited onto alumina of a specific surface area ranging from 50 to 450 m²/g and having a particle size ranging from 20 to 200 microns. The amount of copper chloride, expressed as copper metal, advantageously ranges from 3% to 12% of the total weight of the catalyst.

It is also possible to use catalysts comprising a mixture of the above catalysts and an inert material such as sand. Such catalysts are described in French Patent No. 2,242,143 and European patent No. 377,364.

All of these catalysts are used in a fluidized bed, but it is also within the scope of the invention to utilize fixed bed catalysis.

The reaction temperature advantageously ranges from 220° to 450° C., in consideration that it is necessary to employ a temperature such that the conversion of the CCl₄ does not terminate at the Cl oxychlorinated derivative. The pressure used advantageously ranges from atmospheric pressure to the usual upper limits for this type of process, namely, less than 10 bars.

The reaction is carried out in the presence of oxygen, most advantageously in the form of air.

It is also within the scope of this invention to include hydrochloric acid with the starting materials. The proportions of hydrochloric acid and carbon tetrachloride can vary widely, i.e., the reaction of the invention is between the two reaction schemes (1) and (2).

The feed of air (oxygen) and the feed of ethylene are adjusted to provide almost complete conversion of the ethylene and absence of HCl at the reaction zone outlet. This adjustment is known to the art of oxychlorination.

Advantageously, the proportion of CCl₄ and ethylene is such that the molar ratio $CCl_4/C_2H_4$ ranges from 0.4 to 1.6.

If the reaction is carried out in the presence of HCl, then, in the ratio $CCl_4/C_2H_4$, "CCl₄" represents the sum of the number of moles of CCl₄ and one-quarter of the number of moles of HCl.

Advantageously, the proportion of oxygen and ethylene is such that the molar ratio $O_2/C_2H_4$, the O₂ being expressed as air, ranges from 3 to 10. This indicates that a ratio of 5 signifies one mole of oxygen per mole of ethylene.

In a preferred embodiment of the invention, water vapor is added to the reaction mixture at the inlet to the catalyst bed, namely, the reaction mixture includes C₂H₄, O₂ (air), CCl₄ (optionally with HCl) and H₂O.

The amount of water can vary widely and can range up to 2.5 moles per mole of CCl₄ at the inlet to the catalyst bed.

At the outlet of the catalyst bed, the reaction products are recovered by means well known to the art of oxychlorination, for example cooling and condensing the less volatile products and separating them from the unreacted gases, followed by one or more distillations.

The effect of the water is determined considering that the carbon tetrachloride is hydrolyzed in accordance with the reaction (3):

$$CCl_4 + 2\ H_2O \rightarrow 4HCl + CO_2 \tag{3}$$

after which the HCl thus formed reacts according to the typical reaction (1):

$$2\ C_2H_4 + O_2 + 4\ HCl \rightarrow 2\ C_2H_4Cl_2 + 2\ H_2O \tag{1}$$

In order to further illustrate the present invention and the advantages thereof, the following specific examples are given, it being understood that same are intended only as illustrative and in nowise limitative.

In said examples to follow, the residence times defined as the ratio of the volume of the catalyst (expanded, in the event of oxychlorination conducted in a fluid bed) to the feed rate of the reactants at the inlet to the bed at the reactor temperature are those typically employed in oxychlorination.

EXAMPLE 1

Into a glass reactor of 24 mm diameter, but having a surface area of 4.2412 cm² (allowance having been made for the temperature sheath extending therethrough), of height 1 meter and surmounted by an expansion vessel, there were introduced 160 g of a silica magnesia catalyst (specific surface area, 80 m²/g) impregnated with 3.5% of copper and also containing potassium in an atomic ratio K/Cu of 0.6, and 2.1% of rare earths.

This catalyst is described in French Patent 2,125,748, hereby expressly incorporated by reference. Silica hydrogel microspheres were impregnated with a magnesium chloride solution which was subsequently calcined, after which the powder obtained was impregnated with copper chloride. The bed was maintained at 340° C. by a control system and the following materials were introduced:

| | |
|---|---|
| Air | 1303.1 mmole/hour |
| H₂O | 307.0 mmole/hour |
| CCl₄ | 194.3 mmole/hour |
| C₂H₄ | 152.0 mmole/hour |

The height of the thus fluidized bed was 77 cm and the residence time was on the order of 12 seconds.

The gases exiting the reactor, when cooled to 18° C., deposited 22.9 g of an organic liquid, the composition in % by weight of which was as follows:

| | | |
|---|---|---|
| Dichloroethylene | 0.17 | |
| CHCl₃ | 0.08 | |
| CCl₄ | 30.68 | |
| C₂H₄Cl₂ (D12) | 18.58 | |
| Trichloroethylene (Tri) | 0.74 | |
| C₂H₃Cl₃ AS | 29.33 | AS = Asymmetric |
| Perchloroethylene (Per) | 0.93 | |
| Tetrachloroethane AS | 0.17 | |
| Tetrachloroethanes S | 15.82 | S = Symmetric |
| Pentachloroethane | 3.4 | |
| Hexachloroethane | 0.1 | |

The gas exiting after condensation 31.27 Nliter contained 9.2% by volume of CO₂ and 12% by volume of oxygen. It was free of ethylene and was saturated with solvent at the temperature of 18° C.

The degree of conversion of the CCl₄ was 50% and that of the ethylene was 99.8%.

EXAMPLE 2

The same reactor as described in Example 1 was used, but it was supplemented with measuring instruments typically employed industrially on-line in respect of the gases exiting oxychlorination reactors. The reactants, namely, air, hydrochloric acid, ethylene and carbon tetrachloride, were then introduced onto the same catalyst as described in Example 1. The operating conditions, temperature, residence time and inlet flow rate of the reactants, as well as the flow rates of the excess reactants and of the products formed are reported in the Table below under the heading Example 2. The degree of conversion of the CCl₄ was 47%, that of the ethylene was 99.8% and that of the oxygen was 79.7%.

EXAMPLES 3 AND 4

Using the apparatus described in Example 1, supplemented with the analytical instruments indicated in Example 2, two fresh experiments were carried out, of which the working conditions, entry flow rates of the reactants and exit flow rates of the excess reactants and of the products formed are reported in the following Table under the headings Example 3 and 4.

By way of an example not according to the invention, the following flowstreams were introduced onto the same catalyst as in Example 1, and at a temperature of 340° C.: air 1,303 mmole/H, CCl₄ 182 mmole/H, H₂O 394 mmole/H; at a residence time of 11 seconds, a CCl₄ conversion of 39% was observed.

TABLE:

| Examples | 2 | 3 | 4 |
|---|---|---|---|
| Reactor temperature | 338.7 | 341.5 | 300 |
| Residence time in seconds | 9.8 | 10.1 | 17.2 |
| Inlet flow rate in mmol/h | | | |
| Air | 1,303 | 1,303 | 928.6 |
| HCl | 575 | 0 | 0 |
| CCl₄ | 50 | 233.8 | 219.6 |
| H₂O | 0 | 489 | 0 |

TABLE:-continued

| Examples | 2 | 3 | 4 |
|---|---|---|---|
| $C_2H_4$ | 304 | 304 | 165.2 |
| Outlet flow rate in mmol/h | | | |
| Di + lights | 5.01 | 9.0 | 1.39 |
| $HCCl_3$ | 1.81 | 1.91 | 0.16 |
| $CCl_4$ | 3.42 | 128.3 | 152.22 |
| Tri | 1.15 | 0.23 | 0 |
| T112 | 43.9 | 6.82 | 3.36 |
| PER | 0.31 | 0.10 | 0.036 |
| T4S | 10.98 | 0.3 | 0.198 |
| Penta | 0.9 | 0 | 0.015 |
| D12 | 226 | 184.0 | 124.2 |
| $CO_2$ Total | 33.6 | 211.1 | 137.8 |
| $CCl_4$ | 23.5 | 105.5 | 67.4 |
| CO | 3.1 | 16.7 | 6.2 |
| $C_2H_4$ | ≦0.5 | 41.7 | 4.4 |
| $O_2$ | 55.2 | 0 | 26.25 |
| $N_2$ (analysis) | 1,027 | 1,032 | 699 |
| HCl | 7.15 | 6.4 | 1.75 |
| Degree of conversion | | | |
| $CCl_4$ % | 4.7 | 45.1 | 30.7 |
| $C_2H_4$ % | 99.8 | 86.3 | 97.3 |
| $O_2$ % | 79.7 | ≃100 | 86.5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

We claim:

1. A process for the preparation of 1,2-dichloroethane, consisting essentially of contacting carbon tetrachloride, ethylene and oxygen with a catalytically effective amount of an oxychlorination catalyst at an elevated temperature, and thereafter separating said 1,2-dichlorethane from the products of such oxychloriantion reaction.

2. The process as defined by claim 1, wherein said oxychlorination catalyst comprises a fluidized bed.

3. The process as defined by claim 1, the starting mixture of oxychlorination further comprising HCl.

4. The process as defined by claim 1, the starting mixture of oxychlorination further comprising water vapor.

5. The process as defined by claim 1, carried out at a temperature ranging from 220° C. to 450° C.

6. The process as defined by claim 1, wherein the molar ratio carbon tetrachloride/ethylene ranges from 0.4 to 1.6.

7. The process as defined by claim 1, wherein the molar ratio $O_2/C_2H_4$ ranges from 3 to 10.

* * * * *